United States Patent [19]

Knute

[11] Patent Number: 5,065,010
[45] Date of Patent: Nov. 12, 1991

[54] FIBER OPTIC MEASUREMENT SYSTEM HAVING A REFERENCE CONDUCTOR FOR CONTROLLING THE ENERGY LEVEL OF THE LIGHT SOURCE

[75] Inventor: Wallace L. Knute, Leucadia, Calif.

[73] Assignee: Camino Laboratories, San Diego, Calif.

[21] Appl. No.: 575,351

[22] Filed: Aug. 30, 1990

[51] Int. Cl.⁵ .............................................. H01J 5/16
[52] U.S. Cl. ................................ 250/227.21; 250/205; 250/231.19; 128/667
[58] Field of Search ....................... 250/227.21, 231.19; 128/634, 667, 673, 748; 73/705

[56] References Cited

U.S. PATENT DOCUMENTS

| | | | |
|---|---|---|---|
| 3,051,003 | 8/1962 | Witt | 73/388 |
| 3,249,105 | 5/1966 | Polanyi | 128/2.05 |
| 3,267,932 | 8/1966 | Valliere | 128/2.05 |
| 3,267,932 | 8/1966 | Valliere | 128/2.05 |
| 4,201,222 | 5/1980 | Haase | 128/634 |
| 4,210,029 | 7/1980 | Porter | 73/705 |
| 4,249,076 | 2/1981 | Bergstrom et al. | 250/227 |
| 4,322,978 | 4/1982 | Fromm | 250/231.19 |
| 4,358,960 | 11/1982 | Porter | 73/705 |
| 4,437,206 | 12/1984 | Aagard | 128/667 |
| 4,446,715 | 5/1984 | Bailey | 73/1 |
| 4,588,886 | 5/1986 | Snider | 250/227.21 |
| 4,599,711 | 7/1986 | Cuomo | 250/227.21 |
| 4,805,630 | 2/1989 | Stoney | 128/675 |

Primary Examiner—David C. Nelms
Assistant Examiner—S. Allen
Attorney, Agent, or Firm—Fulwider Patton Lee & Utecht

[57] ABSTRACT

A source fiber receives light from a light source and conducts the light through a catheter to transmit the light to a reflective surface at the catheter end. The reflective surface has a predetermined range of movement and forms a reflected beam from the light transmitted by the source fiber. A reference fiber is located such that it is entirely within the reflected beam throughout the entire range of movement of the reflective surface and its output is substantially constant throughout that range of movement. The output of the reference fiber is used to adjust the light output of the light source. A signal fiber is located such that it is covered by the reflected beam to an extent which is dependent upon the position of the reflective surface in its range of movement. The light output of the signal fiber changes by a relatively large amount through the range of movement of the reflective surface and its output may be used to determine the position of the reflective surface.

24 Claims, 3 Drawing Sheets

FIBER OPTIC MEASUREMENT SYSTEM HAVING A REFERENCE CONDUCTOR FOR CONTROLLING THE ENERGY LEVEL OF THE LIGHT SOURCE

BACKGROUND

The invention is related generally to measuring systems and more particularly, to pressure measuring systems using optical fibers.

The measurement of blood pressure and other physiological pressures is an important technique in modern health care. The intravascular measurement of blood pressure results not only in the accurate measurement of the diastolic and systolic pressures produced in other techniques but also produces the entire pressure waveform. Many pressure measurement devices include a catheter having a tip containing a pressure transducer. Extending through the catheter body are conductors for conducting the pressure data signals from the transducer. At its proximal end, the catheter is coupled to equipment for processing the pressure data signals provided by the catheter tip into a visual display and into written records, if desired, for immediate or future use. In some catheters, the conductors comprise light guides which are referred to herein as optical fibers.

Optical fiber systems offer several advantages. For example, optical fibers are of relatively small size, they are immune to electromagnetic interference, and their cost is relatively low. These advantages make them attractive for use in medical applications, especially where disposability is desired.

In some prior pressure sensor systems, the catheter includes a diaphragm in its tip which moves in some manner in response to the patient's pressure. The diaphragm itself may have a light reflective surface or may be coupled to a light reflective surface which moves in response to diaphragm movement. Typically, in a two fiber system, two optical fibers traverse the catheter, one of which is a source fiber which emits light for reflection by the diaphragm-related reflector and another of which is a signal fiber which receives the reflected light. By measuring the amount of reflected light recieved by the signal fiber, the position of the diaphragm can be determined and, from this, the pressure can be derived.

When subjected to bending, many optical fibers will attenuate conducted light; that is, a significant amount of light is conducted out of the fiber near the bend, thus less light is conducted out of its end. This could cause less light to be emitted from the source fiber, less reflected light to reach the signal fiber and less reflected light to reach the processing equipment. Likewise, a light source which emits more or less light during periods of temperature change, electrical power changes, aging, or under other conditions may result in less reflected light from the reflective surface and less light received by the signal fiber. These changes may be interpreted as pressure changes and result in inaccurate measurements unless some type of compensation system is provided.

One prior compensation system involves the use of two additional fibers traversing the catheter which are coupled together at the transducer end of the catheter. One such fiber is the reference-source fiber and it is coupled at its proximal end to the same light source as the source fiber. The other such fiber is a reference-signal fiber which receives the light directly from the reference-source fiber at the transducer end; that is, the light is not first reflected by the diaphragm but is directly coupled from the reference-source fiber to the reference-signal fiber. These reference fibers would experience any bending and other conditions experienced by the actual signal and source fibers of the catheter and their signals may be used to compensate for such adverse conditions. While this system results in greatly improved accuracy, such an arrangement poses some manufacturing difficulties and increased expense. A catheter with four fibers is generally more expensive and difficult to manufacture than one with three fibers. Additionally, shorting the two reference fibers together in the vicinity of the transducer poses some manufacturing difficulties and expense. Such a catheter also is larger in size; i.e., diameter, to accommodate four fibers and because of the four fibers, is less flexible.

Another prior technique involves the use of only three fibers. Two fibers are used as the source and signal fibers as in the above technique. The third fiber is a reference-signal fiber which extends throughout the catheter as do the other two fibers and is used to compensate for any bending effects and other adverse conditions experienced by the other fibers. In this technique, a moveable diaphragm at the catheter tip is used to reflect light from the source fiber to the signal fiber and a stationary reflective surface also located at the catheter tip is used to reflect a portion of the source fiber's light to the reference-signal fiber. While accuracy is improved over the prior two-fiber approach, fabricating this second reflective surface in the catheter results in manufacturing difficulties and increased expense.

Hence those concerned with the development, manufacture and use of measurement systems have recognized the need for an improved measurement system using fewer optical fibers while still providing a means for compensating for light source output variations and other conditions which cause light variations which may result in inaccurate measurements. Additionally, those concerned have also recognized a need for a measurement system which is easier and less expensive to manufacture. The present invention fulfills these needs.

SUMMARY OF THE INVENTION

Briefly and in general terms, the present invention provides a fiber optic measurement system having three optical fibers, one of which is a source fiber for conducting light from a light source and emitting that light towards a movable reflective surface such as one which may be formed on a movable diaphragm used to sense pressure changes. The reflective surface forms a reflected beam from the emitted light. The second and third fibers are a reference fiber and a signal fiber respectively for receiving the reflected beam. The reference fiber and signal fiber are located at different positions in relation to the reflected beam so that their responses to the reflected beam are different. Although both the reference and signal fibers receive the reflected beam, the reference fiber is relatively insensitive to reflected beam intensity changes caused by movement of the reflective surface while the signal fiber is relatively sensitive thereto.

In one embodiment, the reference fiber is located such that it is entirely within the reflected beam throughout the entire range of movement of the reflective surface while the signal fiber is located such that the amount that it is covered by the reflective beam is dependent upon the position of the reflective surface. In one embodiment, the reference fiber was located between the source fiber and the signal fiber. The light output of the reference fiber is compared to a reference value and if different, an error signal is generated to increase or decrease its light output accordingly.

Although the position of the reference fiber is selected so that it will be relatively insensitive to movement of the reflective surface, it may not have a constant output over the entire range of movement of the reflective surface. If not corrected, the light source output would be caused to increase and decrease in response to the reference fiber changes and such light output changes may be incorrectly interpreted as pressure changes. In accordance with the invention, a characterization system is included which is used to correct the output of the signal fiber for changes in the intensity of the light source caused by the light output variances of the reference fiber over the movement range of the reflective surface.

These and other features and advantages of the invention will become apparent from the following more detailed description, when taken in conjunction with the accompanying drawings of illustrative embodiments.

DESCRIPTION OF THE PREFERRED EMBODIMENTS

Figure 1:
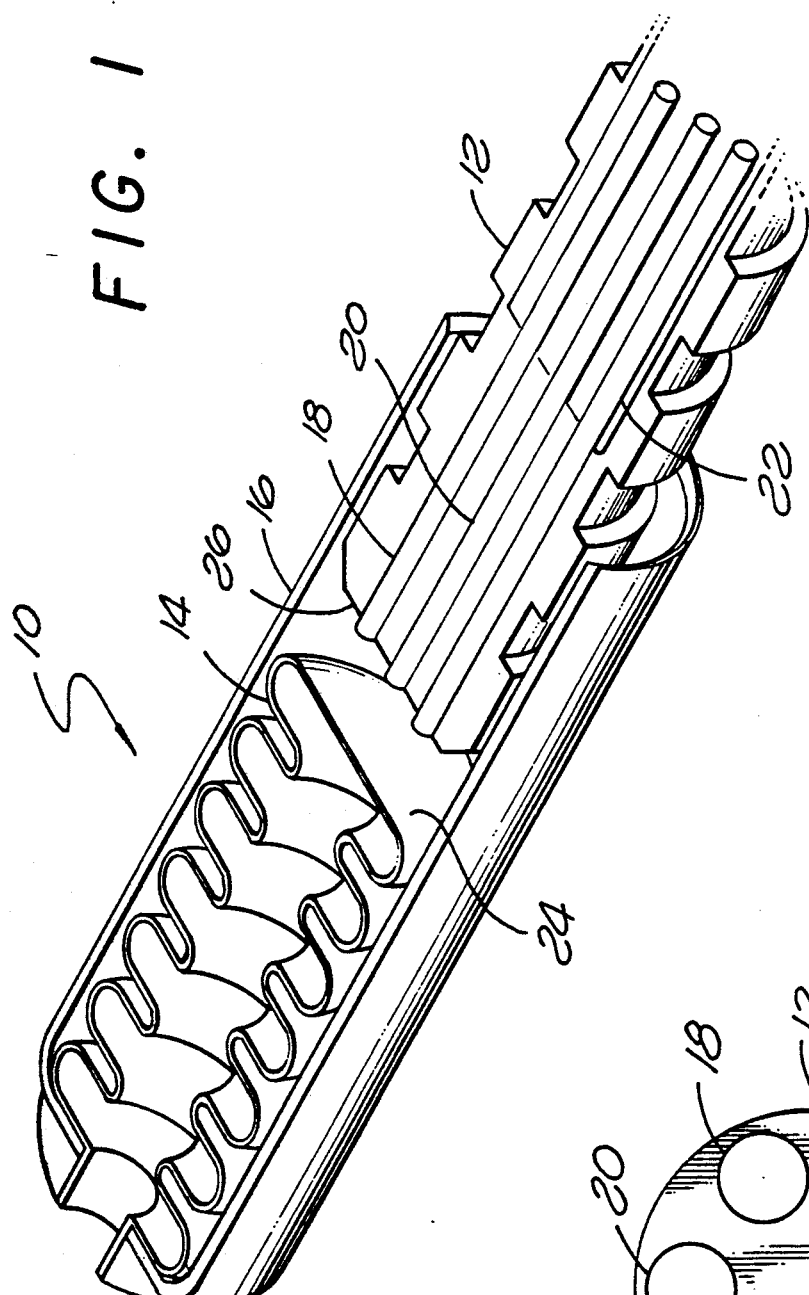
FIG. 1 is a perspective cut-away view of a catheter having a movable diaphragm with a reflective surface in its tip and three optical fibers feeding the diaphragm in accordance with the principles of the invention.

In the following description, like reference numerals will be used to refer to like or corresponding elements in the different figures of the drawings. Referring now to the drawings with more particularity, in FIG. 1 there is shown a catheter 10 with a body section 12 and a bellows-type diaphragm 14 located in its tip 16. In the catheter 10 are disposed three optical fibers, one of which is a source fiber 18, a second of which is a reference fiber 20 and a third of which is a signal fiber 22. The source fiber 18 is used to emit light in the direction of the diaphragm 14 for reflection by a reflective surface 24 coupled to the diaphragm 14 which, in this case, was formed on the diaphragm and is a flat surface. A reflected beam is formed by this reflection. In response to pressure, the reflective surface moves toward and away from the fibers. In FIG. 1, the reference fiber 20 is shown as being disposed adjacent the source fiber 18 and the signal fiber 22 is disposed adjacent the reference fiber 20 on the opposite side thereof from the source fiber 18. In the embodiment shown in FIG. 1, all fibers terminate adjacent the diaphragm approximately in the same plane 26.

In accordance with the principles of the invention, the locations of the reference fiber and signal fiber are selected so that the fibers will have different responses to the reflected beam. While the reference fiber is located so as to be relatively insensitive to reflected beam intensity changes, the signal fiber is located so as to be relatively sensitive thereto.

Figure 2:
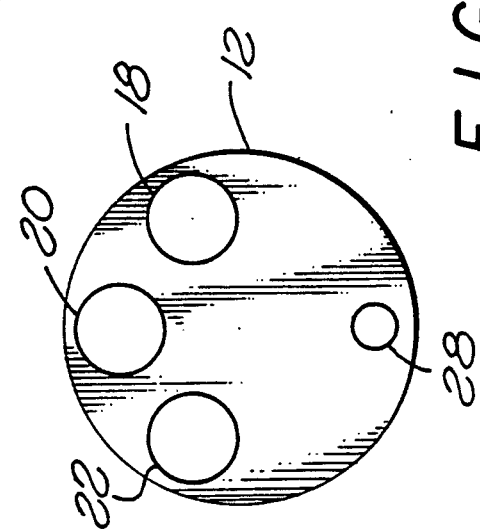
FIG. 2 is an end-on view of three fibers adjacent the diaphragm in accordance with the principles of the invention.

Referring now to FIG. 2, there is shown a cross-sectional view of the catheter body 12 showing the source fiber 18, reference fiber 20, the signal fiber 22 and a vent opening 28. In this example, the reference fiber 20 is located closer to the source fiber 18 than the signal fiber 22, and is located between them. This relative displacement between the fibers results in the reference fiber 20 and the signal fiber 22 receiving different amounts of reflected light. As is discussed in more detail below, in one embodiment the reference fiber 20 is located adjacent the source fiber 18 and its distal end is always within the reflected beam of light over the entire range of movement of the reflective surface 24. The signal fiber 22 is displaced farther from the source fiber 18 and the amount that the reflected beam covers its distal end is dependent upon the position of the reflective surface 24. This is shown in more detail in FIGS. 3A and 3B.

Figure 3A:
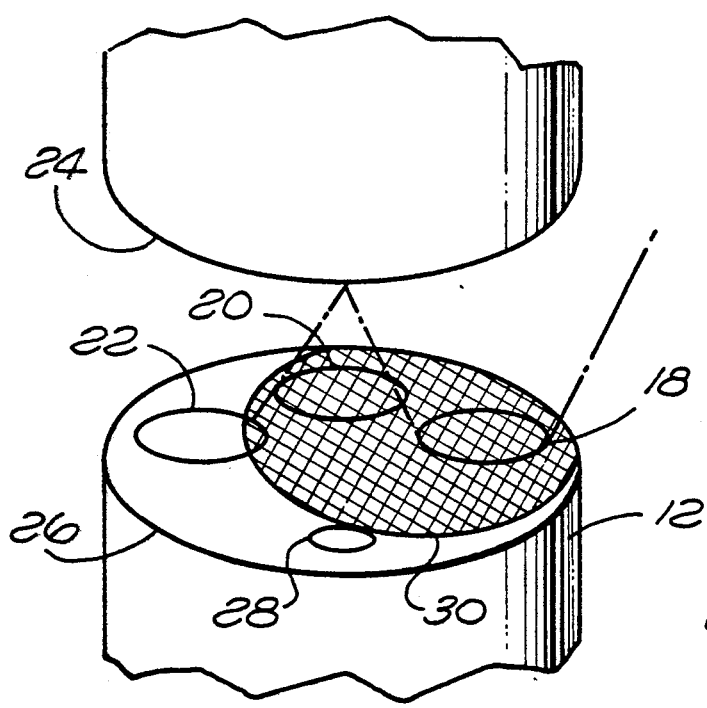
FIGS. 3A and 3B show the pattern of the reflected beam on a surface that is common to the fiber ends when the reflective surface is relatively close to the surface of the fiber ends and when the reflective surface is relatively far from the surface respectively.

In FIG. 3A, due to high sensed pressure, the reflective surface 24 is located relatively close to the plane or surface 26 at which all three optical fibers 18, 20 and 22 terminate. The light emitted to the reflective surface 24 by the source fiber 18 is reflected into a reflected beam and forms the beam pattern 30 on the fiber termination surface 26. The reference fiber 20 is completely covered by the beam pattern 30; however, only a small portion of the signal fiber 22 end is covered.

Figure 3B:
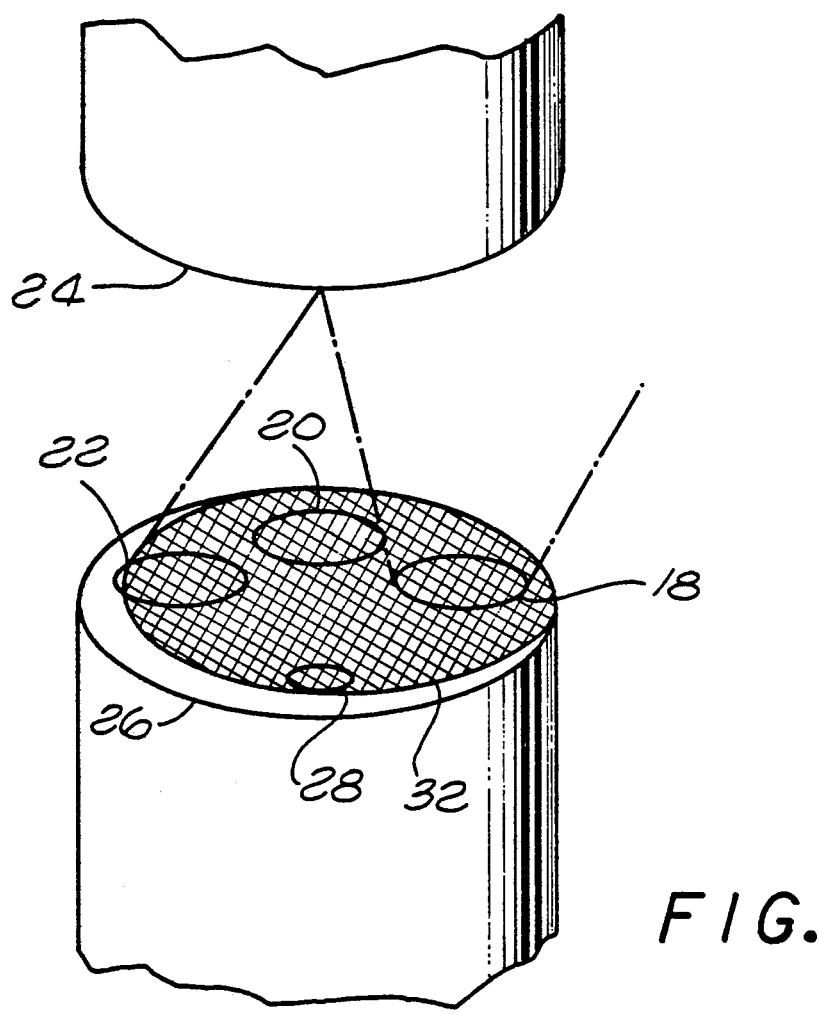

In FIG. 3B, the reflective surface 24 is disposed farther away from the termination surface 26 than in FIG. 3A due to lower sensed pressure. In this case, the reflected beam pattern 32 is larger than the beam pattern 30 in FIG. 3A and covers more of the signal fiber 22. As in FIG. 3A, the reference fiber 20 remains fully covered by the reflected beam pattern 32.

In a preferred embodiment as shown in FIGS. 3A and 3B, the reference fiber 20 remains completely covered by the reflected beam pattern through the entire range of movement of the reflective surface. However, the signal fiber 22 is displaced from the source fiber 18 by a larger distance so that coverage of the signal fiber 22 by the reflected beam pattern is dependent upon the position of the reflective surface 24. Thus in the examples shown in the figures, the signal fiber 22 is covered less when the reflective surface is closer and is covered more when the reflective surface is further away.

In a preferred embodiment, the positions of the fibers in relation to one another, their proximity to the reflective surface and the intensity of the light source are selected so that certain light responsivities of the reference and signal fibers result. In the case of the signal fiber 22, operation in a sensitive range is desired so that a substantial change in light output from the signal fiber 22 occurs in response to reflective surface 24 movement. However, in the case of the reference fiber 20, operation in an insensitive range is desired where very little change in light output occurs in response to reflective surface movement. This feature is shown in further detail in FIG. 4 which is a graph of light outputs of the fibers versus reflective surface position.

Figure 4:
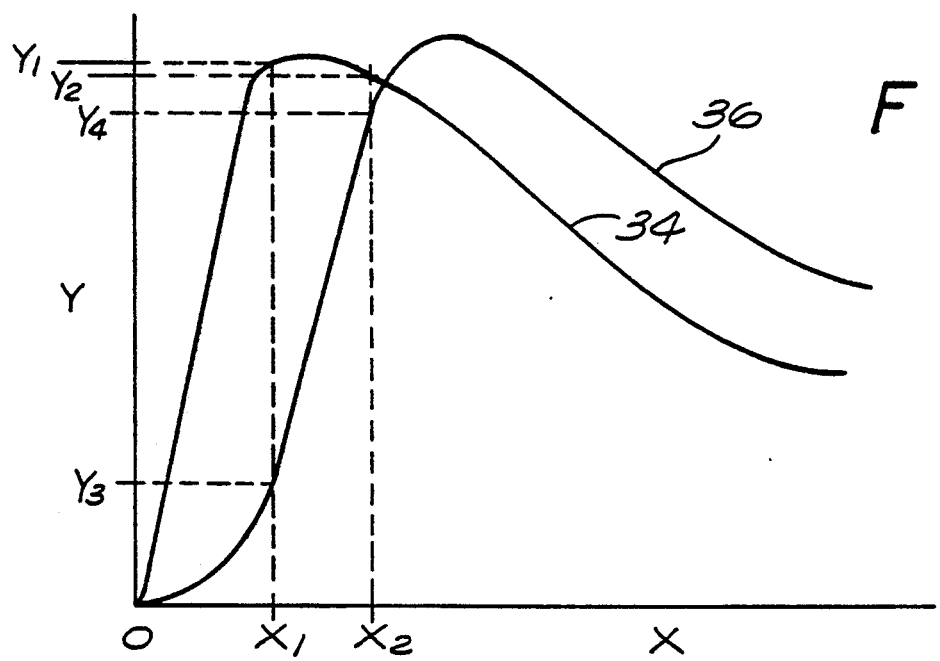
FIG. 4 is a graph showing the displaced curves of the reference fiber and the signal fiber in the sensor in accordance with the principles of the invention.

In FIG. 4, the abscissa (X) represents the distance between the distal ends of the optical fibers and the reflective surface 24 and the ordinate (Y) represents light output at the proximal ends of the reference and signal fibers. Curve 34 represents the light output of the reference fiber 20 and curve 36 represents the light output of the signal fiber 22. As is shown by the curves, when the reflecting surface 24 is at a distance $X=0$; that is, in a position where there is no distance between the fiber ends and the reflecting surface 24, no light output from the fibers occurs. In this position, there is no space for reflection of the source fiber's emitted light to the other fibers. As the distance between the fiber ends and the reflective surface 24 increases, the reference fiber 20 will receive reflections of the source fiber beam first because it is closer to the source fiber 18. As the reflecting surface moves farther away from the fibers, the light outputs of both fibers increase until respective points are reached where light output begins decreasing with increasing distance from the reflective surface.

In FIG. 4, the movement range of the reflective surface 24 in this embodiment is from $X_1$ to $X_2$. In that movement range, the light output of the reference fiber 20 shown by curve 34 changes from $Y_1$ to $Y_2$ while the light output of the signal fiber 22 shown by curve 36 changes from $Y_3$ to $Y_4$. The part of the reference fiber response curve 34 between points $Y_1$ and $Y_2$ is around the peak of the response curve 34 and is in a relatively insensitive range. The light output by the reference fiber 20 changes by a relatively small amount over the range of movement of the reflective surface. However, the part of the signal fiber response curve 36 between points $Y_3$ and $Y_4$ is on the leading edge of the response curve in a sensitive range. The light output of the signal fiber 22 changes by a relatively large amount in response to movement of the reflective surface 24. Thus, changes in position of the reflective surface 24 have little effect on the output of the reference fiber 20 but they have a substantial effect of the light output of the signal fiber 22. Because the reference fiber is co-located with the other fibers, it will experience bending and the other conditions experienced by the other fibers. Because it also receives the reflected beam, its output is an indication of light source output variations also. Thus its output may be used to control the light source to compensate for such conditions as will be discussed in more detail below.

In selecting the initial, or no-pressure position of the reflecting surface 24 in relation to the fiber ends, consideration is given to the expected range of movement of the reflecting surface 24. In one embodiment, the fiber termination plane 26 is moved away from the reflective surface 24 until a peak in light output of the signal fiber 22 is sensed. The reflective surface is then moved closer to the fiber ends until the 50% point of the peak output is reached. However, techniques for the initial placement of the reflective surface may vary.

Figure 5:
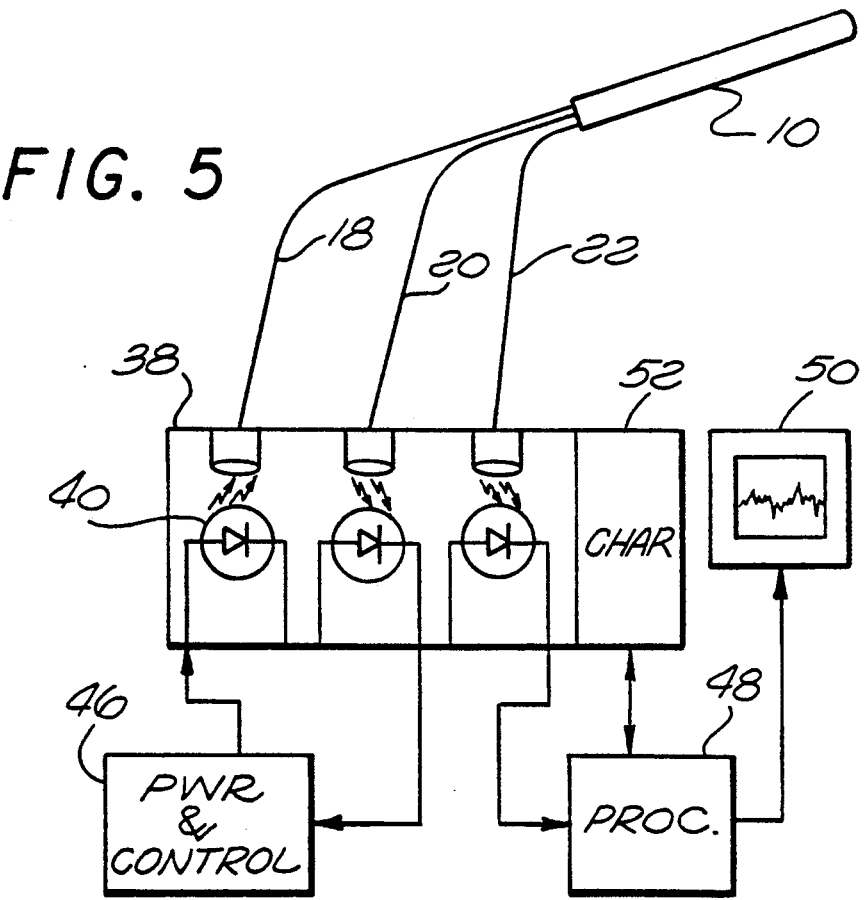
FIG. 5 is a block diagram of the electrical interconnections of a pressure system incorporating the principles of the invention.

Referring now to FIG. 5, the three fibers 18, 20, 22 of the catheter 10 are connected to a coupling block 38 which contains a light source 40 such as a light emitting diode (LED), and two light sensitive transducers 42 and 44 such as photodiodes. In one embodiment, optical fibers having a high numerical aperture were used. The LED 40 is powered by power supply 46 to produce light for use by the source fiber 18. This light is conducted to the catheter and to the pressure transducer for reflection based on the pressure sensed. The reference fiber 20 returns a signal as described in the preceding paragraphs and this light signal is provided to photodiode 42. The signal developed by photodiode 42 is input to the power supply 46 for control thereover. This signal is used to cause the power supply 46 to maintain a constant light level at the photodiode 42. This control may be accomplished by techniques well known to those skilled in the art. For example, the power control may include a differential amplifier which compares the signal from photodiode 42 to a reference voltage. If the signal from photodiode 42 is higher or lower than the reference voltage, the output of power supply 46 is adjusted accordingly.

The signal fiber 22 receives reflected light from the catheter 10 transducer as also described above and that light is coupled from the proximal end of the fiber 22 in the coupling block 38 to photodiode 44. The signal from the photodiode 44 is coupled to a processor 48 for use in deriving pressure based on the position of the reflective surface 24. From the processor 48, a video signal may be generated for display such as by a cathode ray tube 50 or a print or plot signal may be generated for providing written records of the measured pressures.

The processor 48 also calibrates the output of the signal fiber 22 to compensate for intensity changes in the light source caused by changes in the reference fiber output. Even though the relative position of the reference fiber 20 is such that it is relatively insensitive to intensity changes in the reflected beam caused by reflective surface movement, its response may not be constant and may not be linear. This is indicated in FIG. 4 where the points $Y_1$ and $Y_2$ are not equal and do not even define the entire range of light output of the reference fiber between $X_1$ and $X_2$. This variation in response will be reflected in the signal fiber output and without a compensation system, such variation may be incorrectly interpreted as pressure changes. Thus a characterization technique is employed to characterize the change in light output of the reference fiber over the range of reflective surface movement. This characterization function may be accomplished by techniques known to those skilled in the art such as the technique of U.S. Pat. No. 4,446,715 to Bailey. The characterization may be implemented by the use of a bar code, an array of resistors, a programmable memory, a read only memory or by other means which may be located on the coupling block or elsewhere.

As an example, in calibrating the signal fiber output for intensity changes caused by reference fiber output changes, the processor would read the characterization code from the characterizer 52 mounted in the catheter itself and then adjust the signal fiber output accordingly. Such code may provide for characterization of the slope and linearity of the reference fiber output signal for example. In one embodiment, the processor may receive the characterization code and calculate a look-up table on a point by point basis. In another embodiment, the characterizer may comprise a read only memory which stores a point by point look-up table.

A measurement system in accordance with the invention is easier to manufacture, more reliable and is less expensive than many prior systems because it uses no optical focal elements. Compensation for all optical error sources is provided including compensation for degradation of the reflective surface. Degraded reflection by the reflective surface is indicated by a lower output from the reference fiber and in response, the intensity of the light source is increased to compensate. Because the only optical elements are the fibers and the reflective surface, initial calibration of the system is performed simply by setting the spacing between the fibers and the reflective surface. Characterization may be performed and the characterizer installed during manufacture of the measurement system thus making it unnecessary to precisely control the placement of the fibers in relation to each other. A measurement system in accordance with the invention is economical to manufacture and facilitates one-time use and disposability. Although it is disposable, it is highly accurate due to the use of a characterizer.

Thus the invention has provided a new and useful pressure measurement system using only three fibers. All fibers may be terminated in the same plane in the tip of the catheter thus making manufacture easier. Because only three fibers are used, the catheter is less expensive to manufacture, is more flexible than four fiber systems and has improved reliability. No additional reflective devices are needed in the catheter tip thus also contributing to a system in accordance with the invention being less expensive and easier to manufacture.

Although the terms "fiber optics" and "optical fiber" were used herein, the terms were not meant to be used in a restrictive sense and the invention is not restricted to such devices but is applicable to light guides in general. For example, while a single fiber for the source fiber was shown in the drawings, the source fiber may actually comprise a bundle of optical fibers. It may also comprise a light transmitting rod or rods.

It will be apparent from the foregoing that, while particular forms of the invention have been illustrated and described, various modifications can be made without departing from the spirit and scope of the invention. Accordingly, it is not intended that the invention be limited, except as by the appended claims.

What is claimed is:

1. A measurement system comprising:
   a reflective surface having a predetermined range of movement;
   an energy source which provides electromagnetic energy;
   a source conductor which conducts the electromagnetic energy provided by the energy source and emits the conducted energy to the reflective surface for forming a reflected beam;
   a reference conductor displaced from the source conductor by a first distance and which receives and conducts energy of the reflected beam;
   a controller which receives the energy conducted by the reference conductor and controls the level of energy provided by the energy source in response thereto; and
   a signal conductor displaced from the source conductor by a second distance, the second distance being greater than the first distance, and which receives and conducts energy of the reflected beam, and being located such that the amount of energy of the reflected beam conducted varies in accordance with the position of the reflective surface in the predetermined range of movement.

2. The measurement system of claim 1 wherein the reference conductor is disposed between the source conductor and the signal conductor.

3. The measurement system of claim 2 wherein the reference conductor is disposed such that it is entirely covered by the reflected beam throughout the predetermined range of movement of the reflective surface and the signal conductor is disposed such that it is covered by the reflected beam by an amount which varies in relation to the position of the reflective surface in the predetermined range of movement.

4. The measurement system of claim 2 further comprising:
   a characterizer which characterizes the amount of energy conducted by the reference conductor over the predetermined range of movement of the reflective surface; and
   a processor which receives the characterization from the characterizer and receives the energy conducted by the signal fiber and adjusts said energy in response to the characterization.

5. The measurement system of claim 4 wherein:
   the energy source comprises a light source for providing light; and
   the source conductor, the reference conductor and the signal conductor comprise optical fibers.

6. The measurement system of claim 4 wherein the reflective surface is substantially flat.

7. The measurement system of claim 1 wherein the reference conductor is disposed such that it is entirely covered by the reflected beam throughout the predetermined range of movement of the reflective surface and the signal conductor is disposed such that it is covered by the reflected beam by an amount which varies in relation to the position of the reflective surface in the predetermined range of movement.

8. The measurement system of claim 7 wherein the reference conductor is disposed between the source conductor and the signal conductor.

9. The measurement system of claim 8 wherein:
   the reference conductor is disposed such that the amount of energy of the reflected beam that it conducts changes relatively little in response to movement of the reflective surface in the predetermined range of movement; and
   the signal conductor is disposed such that the amount of energy of the reflected beam that it conducts changes by a relatively large amount in response to movement of the reflective surface in the predetermined range of movement.

10. The measurement system of claim 8 wherein the reflective surface is substantially flat.

11. The measurement system of claim 8 further comprising:
    a characterizer which characterizes the amount of energy conducted by the reference conductor over the predetermined range of movement of the reflective surface; and
    a processor which receives the characterization from the characterizer and receives the energy conducted by the signal fiber and adjusts said energy in response to the characterization.

12. The measurement system of claim 11 wherein:
    the energy source comprises a light source for providing light; and
    the source conductor, the reference conductor and the signal conductor comprise optical fibers.

13. The measurement system of claim 1 further comprising:
    a characterizer which characterizes the amount of energy conducted by the reference conductor over the predetermined range of movement of the reflective surface; and
    a processor which receives the characterization from the characterizer and receives the energy conducted by the signal conductor and adjusts said energy in response to the characterization.

14. The measurement system of claim 13 wherein the reflective surface is substantially flat.

15. The measurement system of claim 13 wherein the reference conductor is disposed such that it is entirely covered by the reflected beam throughout the predetermined range of movement of the reflective surface and the signal conductor is disposed such that it is covered by the reflected beam by an amount which varies in relation to the position of the reflective surface in the predetermined range of movement.

16. The measurement system of claim 15 wherein the reference conductor is disposed between the source conductor and the signal conductor.

17. The measurement system of claim 16 wherein:
the energy source comprises a light source for providing light; and
the source conductor, the reference conductor and the signal conductor comprise optical fibers.

18. A measurement system comprising:
a reflective surface having a predetermined range of movement;
a light source which provides light energy;
a source optical fiber which conducts the light provided by the light source and emits the conducted light to the reflective surface for forming a reflected light beam;
a reference optical fiber which receives and conducts light of the reflected light beam;
a controller for receiving the light conducted by the reference fiber and controlling the level of light provided by the light source in response thereto;
a signal optical fiber located such that the reference fiber is between it and the source fiber, and which receives and conducts light of the reflected light beam and being located such that the amount of light of the reflected light beam conducted varies in accordance with the position of the reflective surface in the predetermined range of movement;
a characterizer which characterizes the amount of light conducted by the reference fiber over the predetermined range of movement of the reflective surface; and
a processor which receives the characterization from the characterizer and receives the light conducted by the signal fiber and adjusts said light in response to the characterization.

19. The measurement system of claim 18 wherein the reference fiber is disposed such that it is entirely covered by the reflected beam throughout the predetermined range of movement of the reflective surface and the signal fiber is disposed such that it is covered by the reflected beam by an amount which varies in relation to the position of the reflective surface in the predetermined range of movement.

20. The measurement system of claim 18 wherein:
the reference fiber is disposed such that the amount of energy of the reflected beam that it conducts changes relatively little in response to movement of the reflective surface in the predetermined range of movement; and
the signal fiber is disposed such that the amount of energy of the reflected beam that it conducts changes by a relatively large amount in response to movement of the reflective surface in the predetermined range of movement.

21. The measurement system of claim 18 wherein the reflective surface is substantially flat.

22. A measurement system comprising:
a reflective surface having a predetermined range of movement;
a light source which provides light energy;
a source optical fiber which conducts the light provided by the light source and emits the conducted light to the reflective surface for forming a reflected light beam;
a reference optical fiber displaced from the source fiber by a first distance and which receives and conducts light of the reflected light beam and is disposed such that the amount of energy of the reflected beam that it conducts changes relatively little in response to movement of the reflective surface in the predetermined range of movement;
a controller for receiving the light conducted by the reference fiber and controlling the level of light provided by the light source in response thereto;
a signal optical fiber displaced from the source fiber by a second distance, the second distance being greater than the first distance, and which receives and conducts light of the reflected light beam and which is disposed such that the amount of energy of the reflected beam that it conducts changes by a relatively large amount in response to movement of the reflective surface in the predetermined range of movement;
a characterizer which characterizes the amount of light conducted by the reference fiber over the predetermined range of movement of the reflective surface; and
a processor which receives the characterization from the characterizer and receives the light conducted by the signal fiber and adjusts said light in response to the characterization.

23. The measurement system of claim 22 wherein the reference fiber is located at a position between the source fiber and the signal fiber.

24. The measurement system of claim 22 wherein the reflective surface is substantially flat.

* * * * *